United States Patent
Lee et al.

(10) Patent No.: US 7,256,300 B2
(45) Date of Patent: Aug. 14, 2007

(54) STEREOSELECTIVE SYNTHESIS OF CERTAIN TRIFLUOROMETHYL-SUBSTITUTED ALCOHOLS

(75) Inventors: Thomas Wai-Ho Lee, Danbury, CT (US); John Robert Proudfoot, Newtown, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 403 days.

(21) Appl. No.: 11/081,063

(22) Filed: Mar. 15, 2005

(65) Prior Publication Data
US 2005/0234250 A1    Oct. 20, 2005

Related U.S. Application Data

(60) Provisional application No. 60/557,597, filed on Mar. 30, 2004.

(51) Int. Cl.
*C07D 301/02* (2006.01)
(52) U.S. Cl. .................................................... 549/518
(58) Field of Classification Search ................. 549/518
See application file for complete search history.

(56) References Cited

OTHER PUBLICATIONS

Bravo, P., et al; Synthesis of (-)-(1S,5R) and (+)-(1R,5S)-trifluoroanalogues of frontalin; Tetrahedron Letters 40 (1999)—6317-6320.
Arnone, A., et al; Highly Diastereoselective Methylene Transfer from Diazomethane to the Carbonyl of Keto Sulfoxides. A General Approach to Synthetically Versatile Fluorine-Containing Chiral Building Blocks; Tetrahedrone 54 (1998) 11841-11860.
Ambrose, P., et al: Stereoselective Synthesis of Trifluoro- and Monofluoro-Analogues of Frontalin and Evaluation of their Biologic Activity; J. Org. Chem. 2001, 66, 8336-8343.

*Primary Examiner*—Taofiq Solola
(74) *Attorney, Agent, or Firm*—Michael P. Morris; Mary-Ellen M. Devlin; Timothy X. Witkowski

(57) ABSTRACT

A process for stereoselective synthesis of a compound of Formula (X) or Formula (X')

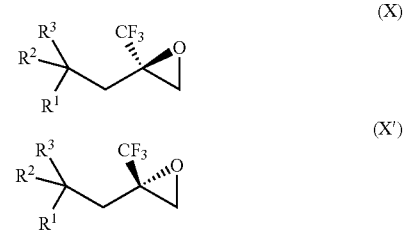

wherein $R^1$, $R^2$, and $R^3$ are as defined herein, the process comprising:
(a) reacting the starting material of formula A with a chiral sulfoxide anion source in a suitable solvent to prepare a compound of formula C or C';
(b) reducing the sulfoxide of formula C or C' in a suitable solvent to obtain the compound of formula D or D'; and
(c) cyclizing the compound of formula D or D' in a suitable solvent to form the epoxide compound of Formula (X) or Formula (X'),
or a tautomer, prodrug, solvate, or salt thereof; pharmaceutical compositions containing such compounds, and methods of modulating the glucocorticoid receptor function and methods of treating disease-states or conditions mediated by the glucocorticoid receptor function or characterized by inflammatory, allergic, or proliferative processes in a patient using these compounds.

15 Claims, No Drawings

STEREOSELECTIVE SYNTHESIS OF CERTAIN TRIFLUOROMETHYL-SUBSTITUTED ALCOHOLS

RELATED APPLICATIONS

This application claims benefit of U.S. Ser. No. 60/557,597, filed Mar. 30, 2004, which is hereby incorporated by reference in its entirety.

FIELD OF THE INVENTION

The present invention relates to the stereoselective synthesis of certain trifluoromethyl-substituted alcohols.

BACKGROUND OF THE INVENTION

Trifluoromethyl-substituted alcohols of formula (I) have been described as ligands that bind to the glucocorticoid receptor. These compounds are potential therapeutics in treating a number of diseases modulated by glucocorticoid receptor function, including inflammatory, autoimmune and allergic disorders. Examples of these compounds are described in U.S. Patent Application Publication Nos. 2003/0232823, 2004/0029932, and 2004/0023999, which are each incorporated herein by reference in their entireties and are hereinafter termed "the Trifluoromethyl-Substituted Alcohol Patent Applications".

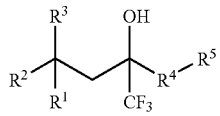

It is well known in the art that enantiomers of a particular compound can have different biological properties including efficacy, toxicity, and pharmacokinetic properties. Thus, it is often desirable to administer one enantiomer of a racemic therapeutic compound.

The synthetic methods disclosed in the patent applications cited above describe the synthesis of racemic products. Separation of enantiomers was accomplished by chiral HPLC and may be accomplished by other conventional ways of separating enantiomers. Chiral HPLC and other enantiomer separation method, however, are generally unsuitable for large-scale preparation of a single enantiomer. Thus, a stereoselective synthesis for preparation of these compounds would be highly desirable.

The present invention discloses a stereoselective synthesis of certain compounds of Formula (X) or (X')

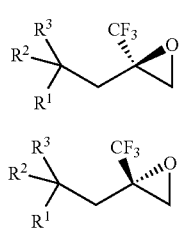

which are key intermediates in the synthesis of enantiomerically pure compounds of Formula (I).

The key step involves a diastereoselective addition of chiral sulfoxide anion to a trifluoromethyl ketone to form a chiral β-hydroxy-β-trifluoromethyl-sulfoxide adduct. In the literature there are limited examples of such diastereoselective addition to fluorinated ketones, e.g., P. Bravo et al., *J. Chem. Soc., Perkin Trans. I* 1995, 1667; P. Bravo et al., *J. Org. Chem.* 1990, 55, 4216; C. Mioskowski and G. Solladie, *Tetrahedron* 1980, 36, 227. In these examples, the authors did not convert these adducts to the corresponding chiral epoxides. A. Arnone et al., *Tetrahedron Lett.* 1996, 37, 3903, describe an enzymatic reduction method for the synthesis of chiral β-hydroxy-β-trifluoromethyl thiol ether and its subsequent conversion to a chiral trifluoromethyl-substituted epoxide.

SUMMARY OF THE INVENTION

The instant invention is directed to a process for stereoselective synthesis of a compound of Formula (X) or Formula (X')

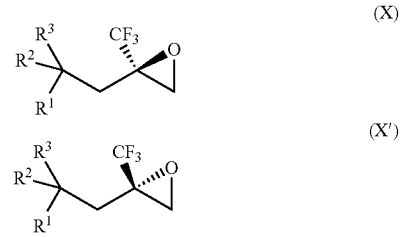

wherein:

$R^1$ is an aryl, heteroaryl, or $C_5$-$C_{15}$ cycloalkyl group, each optionally substituted with one to three substituent groups, wherein each substituent group of $R^1$ is independently $C_1$-$C_5$ alkyl, $C_2$-$C_5$ alkenyl, $C_2$-$C_5$ alkynyl, $C_3$-$C_8$ cycloalkyl, heterocyclyl, aryl, heteroaryl, $C_1$-$C_5$ alkoxy, $C_2$-$C_5$ alkenyloxy, $C_2$-$C_5$ alkynyloxy, aryloxy, acyl, $C_1$-$C_5$ alkoxycarbonyl, $C_1$-$C_5$ alkanoyloxy, $C_1$-$C_5$ alkanoyl, aroyl, aminocarbonyl, alkylaminocarbonyl, dialkylaminocarbonyl, aminocarbonyloxy, $C_1$-$C_5$ alkylaminocarbonyloxy, $C_1$-$C_5$ dialkylaminocarbonyloxy, $C_3$-$C_5$ cycloalkylaminocarbonyloxy, $C_1$-$C_5$ alkanoylamino, $C_1$-$C_5$ alkoxycarbonylamino, $C_1$-$C_5$ alkylsulfonylamino, aminosulfonyl, $C_1$-$C_5$ alkylaminosulfonyl, $C_1$-$C_5$ dialkylaminosulfonyl, halogen, hydroxy, carboxy, cyano, trifluoromethyl, trifluoromethoxy, nitro, or amino wherein the nitrogen atom is optionally independently mono- or di-substituted by $C_1$-$C_5$ alkyl or aryl; or ureido wherein either nitrogen atom is optionally independently substituted with $C_1$-$C_5$ alkyl or $C_3$-$C_5$ cycloalkyl; or $C_1$-$C_5$ alkylthio, wherein each substituent group of $R^1$ is optionally independently substituted with one to four substituent groups selected from aryl or heterocyclyl wherein the heterocycle is optionally independently substituted with hydroxyl, halogen, methyl, or dialkylamino; $C_1$-$C_5$ alkoxycarbonyl, methyl, meth oxy, halogen, hydroxy, oxo, cyano, aminosulfonyl, or amino wherein the nitrogen atom is optionally independently mono- or di-substituted by $C_1$-$C_5$ alkyl or $C_1$-$C_3$ dialkylamine or aryl; or ureido wherein either nitrogen atom is optionally independently substituted with $C_1$-$C_5$ alkyl; or oxime wherein the oxygen atom is optionally substituted by $C_1$-$C_5$ alkyl or benzyl;

$R^2$ and $R^3$ are each independently hydrogen, $C_1$-$C_5$ alkyl, or $C_5$-$C_{15}$ arylalkyl group, or $R^2$ and $R^3$ together with the carbon atom they are commonly attached to form a $C_3$-$C_8$ spiro cycloalkyl ring, or $R^1$ and $R^2$ when taken together are a chromanyl or dihydrobenzofuranyl optionally substituted with $C_1$-$C_5$ alkyl, $C_2$-$C_5$ alkenyl, $C_2$-$C_5$ alkynyl, $C_3$-$C_8$ cycloalkyl, heterocyclyl, aryl, heteroaryl, $C_1$-$C_5$ alkoxy, $C_2$-$C_5$ alkenyloxy, $C_2$-$C_5$ alkynyloxy, aryloxy, acyl, $C_1$-$C_5$ alkoxycarbonyl, $C_1$-$C_5$ alkanoyloxy, aminocarbonyl, alkylaminocarbonyl, dialkylaminocarbonyl, aminocarbonyloxy, $C_1$-$C_5$ alkylaminocarbonyloxy, $C_1$-$C_5$ dialkylaminocarbonyloxy, $C_1$-$C_5$ alkanoylamino, $C_1$-$C_5$ alkoxycarbonylamino, $C_1$-$C_5$ alkylsulfonylamino, aminosulfonyl, $C_1$-$C_5$ alkylaminosulfonyl, $C_1$-$C_5$ dialkylaminosulfonyl, halogen, hydroxy, carboxy, oxo, cyano, trifluoromethyl, trifluoromethoxy, trifluoromethylthio, nitro, or amino wherein the nitrogen atom is optionally independently mono- or di-substituted by $C_1$-$C_5$ alkyl; or ureido wherein either nitrogen atom is optionally independently substituted with $C_1$-$C_5$ alkyl; or $C_1$-$C_5$ alkylthio wherein the sulfur atom is optionally oxidized to a sulfoxide or sulfone, the process comprising:

(a) reacting the starting material of formula A with a chiral sulfoxide anion source B or B', where R is an alkyl or aryl group and M is a counter-cation, in a suitable solvent to prepare a compound of formula C or C', respectively

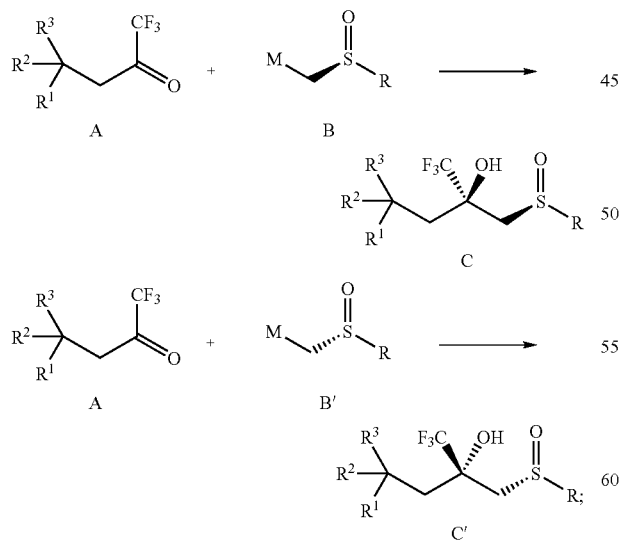

(b) reducing the sulfoxide of formula C or C' in a suitable solvent to obtain the compound of formula D or D', respectively

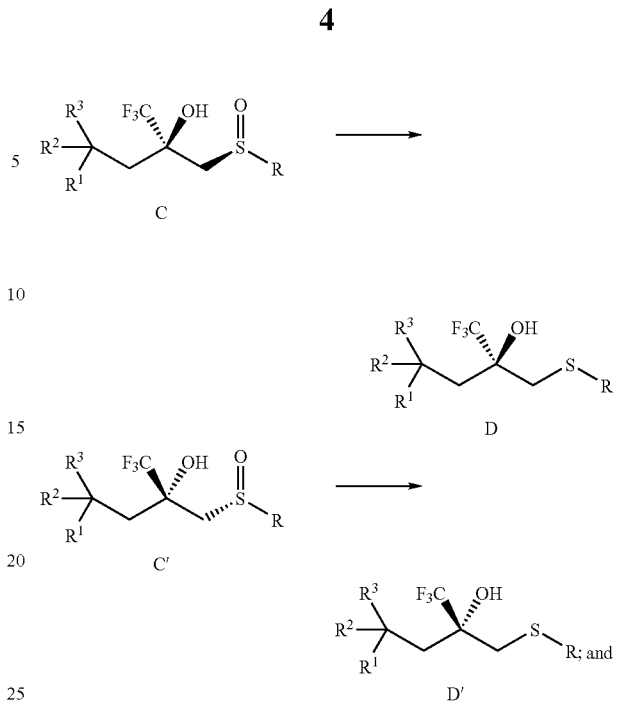

(c) cyclizing the compound of formula D or D' in a suitable solvent to form the epoxide compound of Formula (X) or Formula (X'), respectively

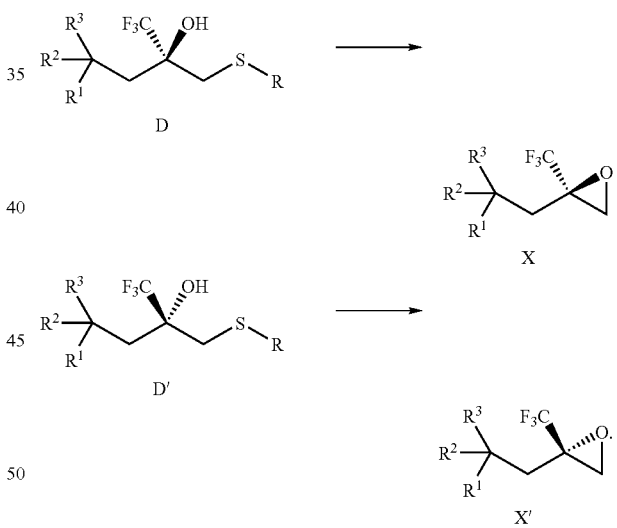

Another aspect of the invention includes a process for stereoselective synthesis of a compound of Formula (X) or Formula (X'), wherein:

$R^1$ is an aryl or heteroaryl group, each optionally substituted with one to three substituent groups, wherein each substituent group of $R^1$ is independently $C_1$-$C_5$ alkyl, $C_2$-$C_5$ alkenyl, $C_2$-$C_5$ alkynyl, $C_3$-$C_8$ cycloalkyl, heterocyclyl, aryl, heteroaryl, $C_1$-$C_5$ alkoxy, $C_2$-$C_5$ alkenyloxy, $C_2$-$C_5$ alkynyloxy, aryloxy, $C_1$-$C_5$ alkanoyloxy, $C_1$-$C_5$ alkanoyl, aroyl, halogen, hydroxy, trifluoromethyl, trifluoromethoxy, or $C_1$-$C_5$ alkylthio, wherein each substituent group of $R^1$ is optionally independently substituted with one to three substituent groups selected from methyl, methoxy, fluoro, chloro, or hydroxy; and $R^2$ and $R^3$ are each independently hydrogen or $C_1$-$C_5$ alkyl, or $R^2$ and $R^3$ together with the carbon atom they are commonly attached to form a $C_3$-$C_8$ spiro cycloalkyl ring, the process as set forth above with $R^1$, $R^2$, and $R^3$ as specified.

In an aspect of the invention, the suitable solvent of step (a) is diethyl ether, dipropyl ether, diisopropyl ether, dibutyl ether, tetrahydrofuran (THF), ethylene glycol dimethyl ether (DME), tert-butyl methyl ether (MTBE), or a mixture thereof, preferably diethyl ether or tetrahydrofuran.

In another aspect of the invention, the chiral sulfoxide anion source B or B' is generated from the corresponding neutral sulfoxide precursor with a base selected from lithium diisopropylamide (LDA), sodium hexamethyldisilazide (NaHMDS), potassium hexamethyldisilazide (KHMDS), sodium hydride, potassium hydride, n-butyllithium, methyllithium, ethyl magnesium bromide, and methylmagnesium bromide.

In yet another aspect of the invention, the reduction of step (b) is accomplished using a reducing agent selected from lithium aluminum hydride (LAH), diisobutyl aluminum hydride (DIBAL), or a 65 wt. % solution of sodium bis(2-methoxyethoxy)aluminum hydride in toluene (Red-Al®), or using other conditions selected from trifluoroacetic acid anhydride/sodium iodide (P. Bravo et al., *J. Org. Chem.*, 1992, 57, 2726), trifluoroacetic acid anhydride/2,4,6-trimethylpyridine (P. Bravo et al., *J. Org. Chem.*, 1990, 55, 4216), or hydrogen chloride in ethanol (J. L. García Ruano et al., *J. Org. Chem.* 1994, 59, 533).

In still another aspect of the invention, when the reduction step (b) is performed with a reducing agent, such as the aluminum hydride reagents listed above, a suitable solvent is diethyl ether, toluene, tetrahydrofuran (THF), tert-butyl methyl ether (MTBE), hexanes, or a mixture thereof. Otherwise, a suitable solvent for step (b) is diethyl ether, toluene, tetrahydrofuran (THF), tert-butyl methyl ether (MTBE), hexanes, benzene, acetonitrile, acetone, dichloromethane, ethyl acetate, or a mixture thereof.

In another aspect of the invention, an alkylating agent is used in step (c), preferably an alkyl halide selected from methyl iodide, methyl bromide, and ethyl iodide, or a trialkyloxonium reagent selected from trimethyloxonium tetrafluoroborate, trimethyloxonium hexachloroantimonate, triethyloxonium tetrafluoroborate, triethyloxonium hexafluorophosphate, and triethyloxonium hexachloroantimonate.

In yet another aspect of the invention, the cyclization of step (c) is accomplished with a suitable organic or inorganic base, preferably triethylamine (TEA), diisopropylethylamine (DIEA), pyridine, lutidine, sodium hydride, potassium hydride, potassium carbonate, or sodium carbonate.

In still another aspect of the invention, the suitable solvent of step (c) is dichloromethane, chloroform, dichloroethane, tetrahydrofuran (THF), diethyl ether, toluene, benzene, ethyl acetate, or a mixture thereof.

In yet another aspect of the invention, this process can be used to prepare the enantiomeric epoxide.

It should be noted that the invention should be understood to include none, some, or all of these various aspects in various combination.

DETAILED DESCRIPTION OF THE INVENTION

Definition of Terms and Conventions Used

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

A. Chemical Nomenclature, Terms, and Conventions

In the groups, radicals, or moieties defined below, the number of carbon atoms is often specified preceding the group, for example, $C_1$-$C_{10}$ alkyl means an alkyl group or radical having 1 to 10 carbon atoms. The term "lower" applied to any carbon-containing group means a group containing from 1 to 8 carbon atoms, as appropriate to the group (i.e., a cyclic group must have at least 3 atoms to constitute a ring). In general, for groups comprising two or more subgroups, the last named group is the radical attachment point, for example, "alkylaryl" means a monovalent radical of the formula Alk-Ar-, while "arylalkyl" means a monovalent radical of the formula Ar-Alk- (where Alk is an alkyl group and Ar is an aryl group). Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups.

The terms "alkyl" or "alkyl group" mean a branched or straight-chain saturated aliphatic hydrocarbon monovalent radical. This term is exemplified by groups such as methyl, ethyl, n-propyl, 1-methylethyl (isopropyl), n-butyl, n-pentyl, 1,1-dimethylethyl (tert-butyl), and the like. It may be abbreviated "Alk".

The terms "alkenyl" or "alkenyl group" mean a branched or straight-chain aliphatic hydrocarbon monovalent radical containing at least one carbon-carbon double bond. This term is exemplified by groups such as ethenyl, propenyl, n-butenyl, isobutenyl, 3-methylbut-2-enyl, n-pentenyl, heptenyl, octenyl, decenyl, and the like.

The terms "alkynyl" or "alkynyl group" mean a branched or straight-chain aliphatic hydrocarbon monovalent radical containing at least one carbon-carbon triple bond. This term is exemplified by groups such as ethynyl, propynyl, n-butynyl, 2-butynyl, 3-methylbutynyl, n-pentynyl, heptynyl, octynyl, decynyl, and the like.

The terms "alkylene" or "alkylene group" mean a branched or straight-chain saturated aliphatic hydrocarbon divalent radical having the specified number of carbon atoms. This term is exemplified by groups such as methylene, ethylene, propylene, n-butylene, and the like, and may alternatively and equivalently be denoted herein as -(alkyl)-.

The terms "alkenylene" or "alkenylene group" mean a branched or straight-chain aliphatic hydrocarbon divalent radical having the specified number of carbon atoms and at least one carbon-carbon double bond. This term is exemplified by groups such as ethenylene, propenylene, n-butenylene, and the like, and may alternatively and equivalently be denoted herein as -(alkylenyl)-.

The terms "alkynylene" or "alkynylene group" mean a branched or straight-chain aliphatic hydrocarbon divalent radical containing at least one carbon-carbon triple bond. This term is exemplified by groups such as ethynylene, propynylene, n-butynylene, 2-butynylene, 3-methylbutynylene, n-pentynylene, heptynylene, octynylene, decynylene, and the like, and may alternatively and equivalently be denoted herein as -(alkynyl)-.

The terms "alkoxy" or "alkoxy group" mean a monovalent radical of the formula AlkO—, where Alk is an alkyl group. This term is exemplified by groups such as methoxy, ethoxy, propoxy, isopropoxy, butoxy, sec-butoxy, tert-butoxy, pentoxy, and the like.

The terms "aryloxy", "aryloxy group", mean a monovalent radical of the formula ArO—, where Ar is aryl. This term is exemplified by groups such as phenoxy, naphthoxy, and the like.

The terms "alkylcarbonyl", "alkylcarbonyl group", "alkanoyl", or "alkanoyl group" mean a monovalent radical of the formula AlkC(O)—, where Alk is alkyl or hydrogen.

The terms "arylcarbonyl", "arylcarbonyl group", "aroyl" or "aroyl group" mean a monovalent radical of the formula ArC(O)—, where Ar is aryl.

The terms "acyl" or "acyl group" mean a monovalent radical of the formula RC(O)—, where R is a substituent selected from hydrogen or an organic substituent. Exemplary substituents include alkyl, aryl, arylalkyl, cycloalkyl, heterocyclyl, heteroaryl, heteroarylalkyl, and the like. As such, the terms comprise alkylcarbonyl groups and arylcarbonyl groups.

The terms "acylamino" or "acylamino group" mean a monovalent radical of the formula RC(O)N(R)—, where each R is a substituent selected from hydrogen or a substituent group.

The terms "alkoxycarbonyl" or "alkoxycarbonyl group" mean a monovalent radical of the formula AlkO—C(O)—, where Alk is alkyl. Exemplary alkoxycarbonyl groups include methoxycarbonyl, ethoxycarbonyl, tert-butyloxycarbonyl, and the like.

The terms "alkylaminocarbonyloxy" or "alkylaminocarbonyloxy group" mean a monovalent radical of the formula $R_2NC(O)O$—, where each R is independently hydrogen or lower alkyl.

The term "alkoxycarbonylamino" or "alkoxycarbonylamino group" mean a monovalent radical of the formula ROC(O)NH—, where R is lower alkyl.

The terms "alkylcarbonylamino" or "alkylcarbonylamino group" or "alkanoylamino" or "alkanoylamino groups" mean a monovalent radical of the formula AlkC(O)NH—, where Alk is alkyl. Exemplary alkylcarbonylamino groups include acetamido ($CH_3C(O)NH$—).

The terms "alkylaminocarbonyloxy" or "alkylaminocarbonyloxy group" mean a monovalent radical of the formula AlkNHC(O)O—, where Alk is alkyl.

The terms "amino" or "amino group" mean an —$NH_2$ group.

The terms "alkylamino" or "alkylamino group" mean a monovalent radical of the formula
(Alk)NH—, where Alk is alkyl. Exemplary alkylamino groups include methylamino, ethylamino, propylamino, butylamino, tert-butylamino, and the like.

The terms "dialkylamino" or "dialkylamino group" mean a monovalent radical of the formula (Alk)(Alk)N—, where each Alk is independently alkyl. Exemplary dialkylamino groups include dimethylamino, methylethylamino, diethylamino, dipropylamino, ethylpropylamino, and the like.

The terms "substituted amino" or "substituted amino group" mean a monovalent radical of the formula —$NR^2$, where each R is independently a substituent selected from hydrogen or the specified substituents (but where both Rs cannot be hydrogen). Exemplary substituents include alkyl, alkanoyl, aryl, arylalkyl, cycloalkyl, heterocyclyl, heteroaryl, heteroarylalkyl, and the like.

The terms "alkoxycarbonylamino" or "alkoxycarbonylamino group" mean a monovalent radical of the formula AlkOC(O)NH—, where Alk is alkyl.

The terms "ureido" or "ureido group" mean a monovalent radical of the formula $R_2NC(O)NH$—, where each R is independently hydrogen or alkyl.

The terms "halogen" or "halogen group" mean a fluoro, chloro, bromo, or iodo group.

The term "halo" means one or more hydrogen atoms of the group are replaced by halogen groups.

The terms "alkylthio" or "alkylthio group" mean a monovalent radical of the formula AlkS—, where Alk is alkyl. Exemplary groups include methylthio, ethylthio, n-propylthio, isopropylthio, n-butylthio, and the like.

The terms "sulfonyl" or "sulfonyl group" mean a divalent radical of the formula —$SO_2$—.

The terms "carbocycle" or "carbocyclic group" mean a stable aliphatic 3- to 15-membered monocyclic or polycyclic monovalent or divalent radical consisting solely of carbon and hydrogen atoms which may comprise one or more fused or bridged ring(s), preferably a 5- to 7-membered monocyclic or 7- to 10-membered bicyclic ring. Unless otherwise specified, the carbocycle may be attached at any carbon atom which results in a stable structure and, if substituted, may be substituted at any suitable carbon atom which results in a stable structure. The term comprises cycloalkyl (including spiro cycloalkyl), cycloalkylene, cycloalkenyl, cycloalkenylene, cycloalkynyl, and cycloalkynylene, and the like.

The terms "cycloalkyl" or "cycloalkyl group" mean a stable aliphatic saturated 3- to 15-membered monocyclic or polycyclic monovalent radical consisting solely of carbon and hydrogen atoms which may comprise one or more fused or bridged ring(s), preferably a 5- to 7-membered monocyclic or 7- to 10-membered bicyclic ring. Unless otherwise specified, the cycloalkyl ring may be attached at any carbon atom which results in a stable structure and, if substituted, may be substituted at any suitable carbon atom which results in a stable structure. Exemplary cycloalkyl groups include cyclopropyl, cyclobutyl, cyclopentyl, cyclohexyl, cycloheptyl, cyclooctyl, cyclononyl, cyclodecyl, norbomanyl, adamantyl, tetrahydronaphthyl (tetralin), 1-decalinyl, bicyclo [2.2.2]octanyl, 1-methylcyclopropyl, 2-methylcyclopentyl, 2-methylcyclooctyl, and the like.

The terms "aryl" or "aryl group" mean an aromatic carbocyclic monovalent or divalent radical of from 6 to 14 carbon atoms having a single ring (e.g., phenyl or phenylene) or multiple condensed rings (e.g., naphthyl or anthranyl). Unless otherwise specified, the aryl ring may be attached at any suitable carbon atom which results in a stable structure and, if substituted, may be substituted at any suitable carbon atom which results in a stable structure. Exemplary aryl groups include phenyl, naphthyl, anthryl, phenanthryl, indanyl, indenyl, biphenyl, and the like. It may be abbreviated "Ar".

The terms "heteroaryl" or "heteroaryl group" mean a stable aromatic 5- to 14-membered, monocyclic or polycyclic monovalent or divalent radical which may comprise one or more fused or bridged ring(s), preferably a 5- to 7-membered monocyclic or 7- to 10-membered bicyclic radical, having from one to four heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heteroaryl ring may be attached at any suitable heteroatom or carbon atom which results in a stable structure and, if substituted, may be substituted at any suitable heteroatom or carbon atom which results in a stable structure. Exemplary and preferred heteroaryls include furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, triazinyl, indolizinyl, azaindolizinyl, indolyl, azaindolyl, diazaindolyl, dihydroindolyl, dihydroazaindoyl, isoindolyl, azaisoindolyl, benzofuranyl, furanopyridinyl, furanopyrimidinyl, furanopyridinyl, furanopyrimidinyl, dihydrobenzofuranyl, dihydrofuranopyridinyl, dihydrofuranopyrimidinyl, benzodioxolanyl, benzothienyl, thienopyridinyl, thienopyrimidinyl, thienopyrazinyl, thienopyridazinyl, dihydrobenzothienyl, dihydrothienopyridinyl, dihydrothienopyrimidinyl, indazolyl, azaindazolyl, diazaindazolyl, benzimidazolyl, imidazopyridinyl, benzthiazolyl, thiazolopyridinyl, thiazolopyrimidinyl, benzoxazolyl, oxazolopyridinyl, oxazolopyrimidinyl, benzisoxazolyl, purinyl, chromanyl, azachromanyl, quinolizinyl, quinolinyl, dihydroquinolinyl, tetrahydroquinolinyl, isoquinolinyl, dihydroisoquinolinyl, tetrahydroisoquinolinyl, cinnolinyl, azacinnolinyl, phthalazinyl, azaphthalazinyl, quinazolinyl, azaquinazolinyl, quinoxalinyl, azaquinoxalinyl, naphthyridinyl, dihydronaphthyridinyl, tetrahydronaphthyridinyl, pteridinyl, carbazolyl, acridinyl, phenazinyl, phenothiazinyl, and phenoxazinyl, and the like.

The terms "heterocycle", "heterocycle group", "heterocyclyl", or "heterocyclyl group" mean a stable non-aromatic 5- to 14-membered monocyclic or polycyclic, monovalent or divalent, ring which may comprise one or more fused or bridged ring(s), preferably a 5- to 7-membered monocyclic or 7- to 10-membered bicyclic ring, having from one to three heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heterocyclyl ring may be attached at any suitable heteroatom or carbon atom which results in a stable structure and, if substituted, may be substituted at any suitable heteroatom or carbon atom which results in a stable structure. Exemplary and preferred heterocycles include pyrrolinyl, pyrrolidinyl, pyrazolinyl, pyrazolidinyl, piperidinyl, morpholinyl, thiomorpholinyl, piperazinyl, tetrahydropyranyl, tetrahydrothiopyranyl, tetrahydrofuranyl, hexahydropyrimidinyl, hexahydropyridazinyl, and the like.

The term "compounds of the invention" and equivalent expressions are meant to embrace compounds of Formula (I) as herein described, including the tautomers, the prodrugs, the salts, particularly the pharmaceutically acceptable salts, and the solvates and hydrates thereof, where the context so permits. In general and preferably, the compounds of the invention and the formulas designating the compounds of the invention are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits.

The terms "optional" or "optionally" mean that the subsequently described event or circumstances may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution.

The terms "stable compound" or "stable structure" mean a compound that is sufficiently robust to survive isolation to a useful degree of purity from a reaction mixture, and formulation into an efficacious therapeutic or diagnostic agent. For example, a compound which would have a "dangling valency" or is a carbanion is not a compound contemplated by the invention.

The term "substituted" means that any one or more hydrogens on an atom of a group or moiety, whether specifically designated or not, is replaced with a selection from the indicated group of substituents, provided that the atom's normal valency is not exceeded and that the substitution results in a stable compound. If a bond to a substituent is shown to cross the bond connecting two atoms in a ring, then such substituent may be bonded to any atom on the ring. When a substituent is listed without indicating the atom via which such substituent is bonded to the rest of the compound, then such substituent may be bonded via any atom in such substituent. For example, when the substituent is piperazinyl, piperidinyl, or tetrazolyl, unless specified otherwise, such piperazinyl, piperidinyl, or tetrazolyl group may be bonded to the rest of the compound of the invention via any atom in such piperazinyl, piperidinyl, or tetrazolyl group. Generally, when any substituent or group occurs more than one time in any constituent or compound, its definition on each occurrence is independent of its definition at every other occurrence. Such combinations of substituents and/or variables, however, are permissible only if such combinations result in stable compounds.

In a specific embodiment, the term "about" or "approximately" means within 20%, preferably within 10%, and more preferably within 5% of a given value or range.

The yield of each of the reactions described herein is expressed as a percentage of the theoretical yield.

EXPERIMENTAL EXAMPLES

The invention provides processes for making compounds of Formula (X) or (X'). In all schemes, unless specified otherwise, $R^1$ to $R^3$ in the formulas below have the meanings of $R^1$ to $R^3$ in the Summary of the Invention section. For synthesis of intermediates, see the synthetic procedures disclosed in U.S. Patent Application Publication Nos. 2004/0023999 and 2004/0162321, which are each incorporated herein by reference in their entireties. Other intermediates used in the preparation of compounds of the invention are either commercially available or readily prepared by methods known to those skilled in the art.

The epoxide of Formula (II) is a key intermediate in the synthesis of certain racemic compounds of Formula (I), as described in U.S. Patent Application Publication No. 2004/

0162321, which is hereby incorporated by reference. Treatment of the epoxide of Formula (II) with the nucleophile R⁵H, in the presence of base opens the epoxide to provide racemic (I) as shown below in Scheme I

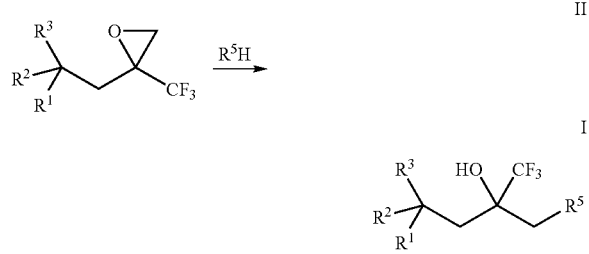

The stereoselective synthesis of a single enantiomer of epoxide (II) is carried out as shown in Scheme II below.

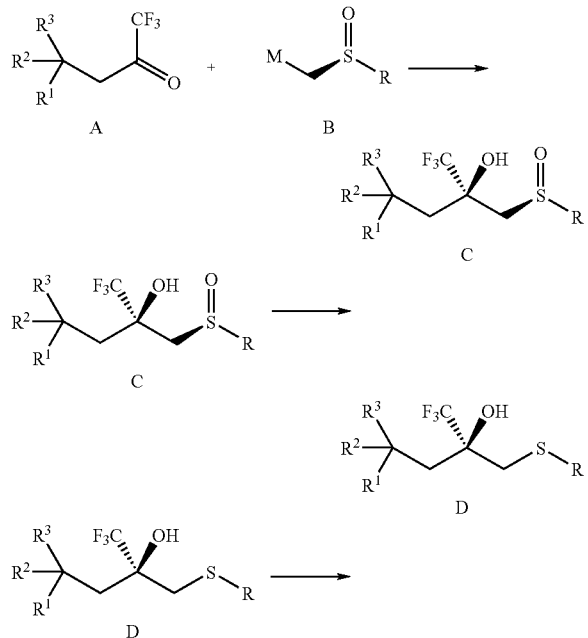

As illustrated in Scheme II, reacting the starting material of formula A with a chiral sulfoxide anion source B in the presence of a suitable base, such as LDA, in a suitable solvent, such as THF, provides a compound of formula C. Reduction of the sulfoxide of formula C with suitable reducing agents affords the compound of formula D. Reaction of the compound of formula D with reagents such as trimethyloxonium tetrafluoroborate in a suitable solvent, such as dichloromethane, in the presence of a suitable base, such as potassium carbonate, provides epoxide of Formula (X). The analogous reaction can be performed to make an epoxide of Formula (X').

Preparation of the desired enantiomer of Formula (I) can then be achieved by reaction of the compound of Formula (X) or Formula (X'), which is enantiomerically pure (II), with the appropriate nitrogen, oxygen, sulfur, or carbon nucleophile (R⁵H) by methods known to those skilled in the art.

Optimum reaction conditions and reaction times may vary depending on the particular reactants used. Unless otherwise specified, solvents, temperatures, pressures, and other reaction conditions may be readily selected by one of ordinary skill in the art. Furthermore, if the substituent groups on $R^1$ to $R^3$ are incompatible under the reaction conditions of the process, protection/deprotection of these groups may be carried out, as required, using reagents and conditions readily selected by one of ordinary skill in the art, see, for example, T. W. Greene and P. G. M. Wuts, *Protective Groups in Organic Synthesist* New York: John Wiley & Sons (1999) and references cited therein. For example, a hydroxyl group can be protected as methyl ether and be deprotected at an appropriate stage with reagents, such as boron tribromide in dichloromethane. Specific procedures are provided in the Experimental Examples section. Typically, reaction progress may be monitored by high performance liquid chromatography (HPLC) or thin layer chromatography (TLC), if desired, and intermediates and products may be purified by chromatography on silica gel and/or by recrystallization.

SYNTHETIC EXAMPLES

The following are representative examples that illustrate the process of the invention. HPLC used to determine diastereoselectivity were done on a Supelco SUPELCO-SIL™ ABZ+Plus column (4.6 mm×10 cm) eluting with a gradient of 5% acetonitrile/95% water/0.05% TFA to 100% acetonitrile/0.05% TFA over 15 minutes and then held at 100% acetonitrile/0.05% TFA for 5 minutes. References to concentration or evaporation of solutions refer to concentration on a rotary evaporator.

Example 1

Synthesis of (R)-2-[2-(5-Fluoro-2-methoxyphenyl)-2-methylpropyl]-2-trifluoromethyloxirane

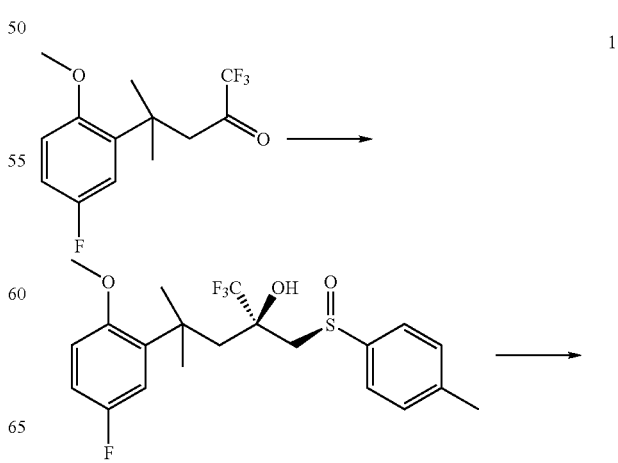

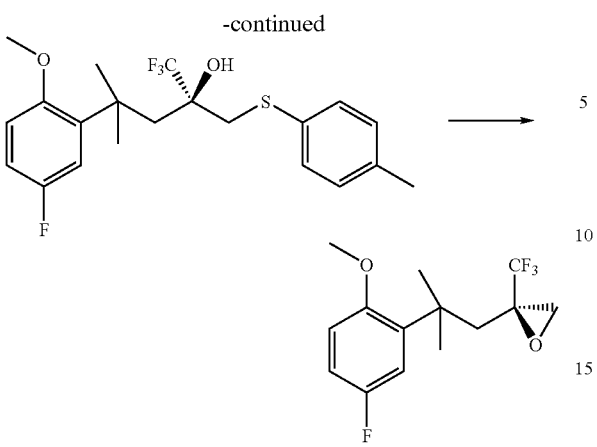

To a suspension of (R)-(+)-methyl p-tolylsulfoxide (28.2 g, 183 mmol) in 200 mL of anhydrous THF at −78° C. was added lithium diisopropylamide (LDA) mono(tetrahydrofuran), 1.5 M solution in cyclohexane (122 mL, 183 mmol) over 30 minutes. The resulting clear yellow solution was stirred for an additional 15 minutes. 1,1,1-Trifluoro-4-(5-fluoro-2-methoxyphenyl)-4-methylpentan-2-one (46.3 g, 166 mmol) dissolved in 125 mL of THF was then added via cannula over 30 minutes. After 1.5 hours at −78° C., the reaction mixture was quenched with 600 mL of water and extracted first with a 600 mL portion of EtOAc and then a 400 mL portion of EtOAc. The combined organic phases were washed with saturated aqueous sodium bicarbonate ($NaHCO_3$) solution, washed with brine, dried over sodium sulfate ($Na_2SO_4$), filtered, and concentrated in vacuo. Purification by column chromatography with silica gel (eluted with 10%-30% EtOAc/hexanes) afforded sequentially (S)-1,1,1-trifluoro-4-(5-fluoro-2-methoxyphenyl)-4-methyl-2-((R)-toluene-4-sulfinylmethyl)pentan-2-ol (44.2 g, 62%) and (R)-1,1,1-trifluoro-4-(5-fluoro-2-methoxyphenyl)-4-methyl-2-((R)-toluene-4-sulfinylmethyl)pentan-2-ol (20.6 g, 29%). The diastereomeric excess was determined to be >99% for both isomers (HPLC peak area).

To a suspension of (S)-1,1,1-trifluoro-4-(5-fluoro-2-methoxyphenyl)-4-methyl-2-((R)-toluene-4-sulfinylmethyl)pentan-2-ol (44.2 g, 102 mmol) and sodium iodide (46.0 g, 307 mmol) in 600 mL of anhydrous acetone at −40° C. was added a solution of trifluoroacetic acid anhydride (72.2 mL, 511 mmol) in 200 mL of anhydrous acetone via an addition funnel dropwise over 30 minutes. A greenish brown mixture was formed instantaneously. After 15 minutes, the reaction mixture was quenched with saturated aqueous sodium sulfite ($Na_2SO_3$) solution and neutralized with saturated aqueous sodium carbonate ($Na_2CO_3$) solution. The brown color disappeared and the crude product was concentrated to remove most of the acetone solvent. The resulting material was diluted with water and extracted three times with ether (one 600 mL portion and two 400 mL portions). The combined organic phases were washed with brine, dried over magnesium sulfate ($MgSO_4$), filtered, and concentrated in vacuo to afford (S)-1,1,1-trifluoro-4-(5-fluoro-2-methoxyphenyl)-4-methyl-2-p-tolylsulfanylmethylpentan-2-ol as an orange oil (42.7 g, 100%).

To a solution of (S)-1,1,1-trifluoro-4-(5-fluoro-2-methoxyphenyl)-4-methyl-2-p-tolylsulfanylmethylpentan-2-ol (42.7 g, 102 mmol) in 250 mL of anhydrous dichloromethane was added trimethyloxonium tetrafluoroborate (22.7 g, 153 mmol). The resulting suspension was stirred at room temperature for 4.5 hours. A solution of potassium carbonate (42.4 g, 307 mmol) in 250 mL of water was then added. After 16 hours, the reaction mixture was poured into 200 mL of saturated aqueous sodium bicarbonate solution and extracted with three 400 mL portions of dichloromethane. The combined organic phases were washed with brine, dried over magnesium sulfate, filtered, and concentrated in vacuo. Purification by column chromatography with silica gel (eluted with 0%-2% EtOAc/hexanes) afforded the title compound as a pale yellow oil (28.3 g, 95%).

Example 2

Synthesis of (R)-2-[2-(5-Fluoro-2-methylphenyl)-2-methylpropyl]-2-trifluoromethyloxirane

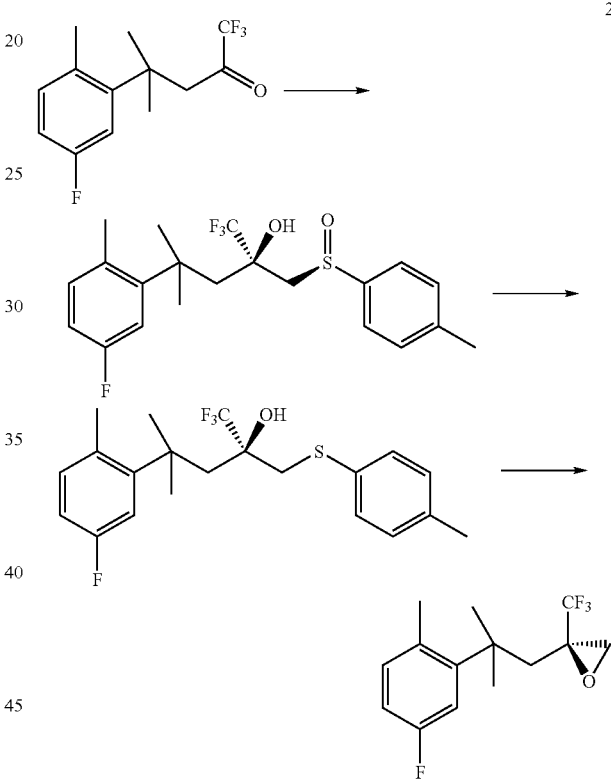

2

To a suspension of (R)-(+)-methyl p-tolylsulfoxide (1.00 g, 6.48 mmol) in 10 mL of anhydrous THF at −78° C. was added LDA mono(tetrahydrofuran), 1.5 M solution in cyclohexane (4.32 mL, 6.48 mmol) over 5 minutes. The resulting clear yellow solution was stirred for an additional 15 minutes. 1,1,1-Trifluoro-4-(5-fluoro-2-methylphenyl)-4-methylpentan-2-one (1.55 g, 5.90 mmol) was then added via cannula with the aid of 4 mL of THF over 5 minutes. After 1 hour at −78° C., the reaction mixture was quenched with 50 mL of water and extracted with three 50 mL portions of EtOAc. The combined organic phases were washed with saturated aqueous sodium bicarbonate solution, brine, dried over sodium sulfate, filtered, and concentrated in vacuo. Purification by column chromatography with silica gel (eluted with 15%-25% EtOAc/hexanes) afforded sequentially (S)-1,1,1-trifluoro-4-(5-fluoro-2-methylphenyl)-4-methyl-2-((R)-toluene-4-sulfinylmethyl)pentan-2-ol (1.42 g, 58%) and (R)-1,1,1-trifluoro-4-(5-fluoro-2-methylphenyl)-

4-methyl-2-((R)-toluene-4-sulfinylmethyl)pentan-2-ol (665 mg, 27%). The diastereomeric excess was determined to be >99% for both isomers (HPLC peak area).

To a suspension of (S)-1,1,1-trifluoro-4-(5-fluoro-2-methylphenyl)-4-methyl-2-((R)-toluene-4-sulfinylmethyl)pentan-2-ol (1.42 g, 3.41 mmol) and sodium iodide (1.53 g, 10.2 mmol) in 25 mL of anhydrous acetone at −40° C. was added a solution of trifluoroacetic acid anhydride (2.41 mL, 17.1 mmol) in 5 mL of anhydrous acetone via a syringe dropwise over 5 minutes. A greenish brown mixture was formed instantaneously. After 15 minutes, the reaction mixture was quenched with saturated aqueous sodium sulfite solution and neutralized with saturated aqueous sodium carbonate solution. The brown color disappeared and the crude was concentrated to remove most of the acetone solvent. The resulting material was diluted with 50 mL of water and extracted with three 100 mL portions of ether. The combined organic phases were washed with brine, dried over magnesium sulfate, filtered, and concentrated in vacuo to afford (S)-1,1,1-trifluoro-4-(5-fluoro-2-methylphenyl)-4-methyl-2-p-tolylsulfanylmethylpentan-2-ol as a yellow oil (1.37 g, 100%).

To a solution of (S)-1,1,1-trifluoro-4-(5-fluoro-2-methylphenyl)-4-methyl-2-p-tolylsulfanylmethylpentan-2-ol (1.37 g, 3.41 mmol) in 10 mL of anhydrous dichloromethane was added trimethyloxonium tetrafluoroborate (757 mg, 5.12 mmol). The resulting suspension was stirred at room temperature for 4.5 hours. A solution of potassium carbonate (1.41 g, 10.2 mmol) in 10 mL of water was then added. After 19 hours, the reaction mixture was poured into 40 mL of saturated aqueous sodium bicarbonate solution and extracted with three 50 mL portions of dichloromethane. The combined organic phases were washed with brine, dried over magnesium sulfate, filtered, and concentrated in vacuo. Purification by column chromatography with silica gel (eluted with 0%-2% EtOAc-hexanes) afforded the title compound as a clear oil (731 mg, 78%).

Example 3

Synthesis of (R)-5-Chloro-7-[1,1-dimethyl-2-(2-trifluoromethyloxiranyl)-ethyl]-2,3-dihydrobenzofuran

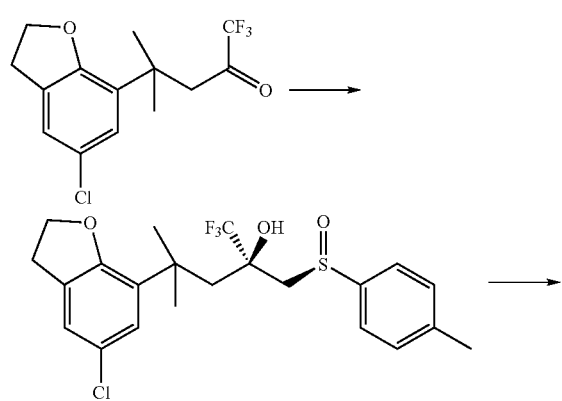

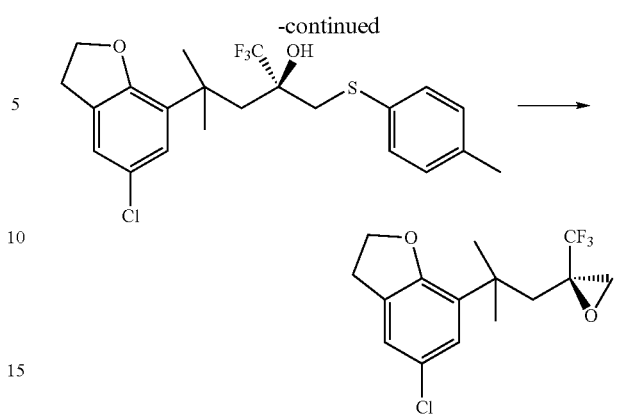

To a suspension of (R)-(+)-methyl p-tolylsulfoxide (1.00 g, 6.48 mmol) in 10 mL, of anhydrous THF at −78° C. was added LDA mono(tetrahydrofuran), 1.5 M solution in cyclohexane (4.32 mL, 6.48 mmol) over 5 minutes. The resulting clear yellow solution was stirred for an additional 15 minutes. 4-(5-Chloro-2,3-dihydrobenzofuran-7-yl)-1,1,1-trifluoro-4-methylpentan-2-one (1.81 g, 5.90 mmol) was then added via cannula with the aid of 4 mL of THF over 5 minutes. After 1 hour at −78° C., the reaction mixture was quenched with 50 mL of water and extracted with three 50 mL portions of EtOAc. The combined organic phases were washed with saturated aqueous sodium bicarbonate solution, brine, dried over sodium sulfate, filtered, and concentrated in vacuo. Purification by column chromatography with silica gel (eluted with 15%-25% EtOAc-hexanes) afforded sequentially (S)-4-(5-chloro-2,3-dihydrobenzofuran-7-yl)-1,1,1-trifluoro-4-methyl-2-((R)-toluene-4-sulfinylmethyl)pentan-2-ol (1.49 g, 55%) and (R)-4-(5-chloro-2,3-dihydrobenzofuran-7-yl)-1,1,1-trifluoro-4-methyl-2-((R)-toluene-4-sulfinylmethyl)pentan-2-ol (670 mg, 25%). The diastereomeric excess was determined to be >99% for both isomers (HPLC peak area).

To a suspension of (S)-4-(5-chloro-2,3-dihydrobenzofuran-7-yl)-1,1,1-trifluoro-4-methyl-2-((R)-toluene-4-sulfinylmethyl)pentan-2-ol (1.49 g, 3.23 mmol) and sodium iodide (1.45 g, 9.70 mmol) in 25 mL of anhydrous acetone at −40° C. was added a solution of trifluoroacetic acid anhydride (2.28 mL, 16.2 mmol) in 5 mL of anhydrous acetone via a syringe dropwise over 5 minutes. A greenish brown mixture was formed instantaneously. After 15 minutes, the reaction mixture was quenched with saturated aqueous sodium sulfite solution and neutralized with saturated aqueous sodium carbonate solution. The brown color disappeared and the crude was concentrated in vacuo to remove most of the acetone solvent. The resulting material was diluted with 50 mL of water and extracted with three 100 mL portions of ether. The combined organic phases were washed with brine, dried over magnesium sulfate, filtered, and concentrated in vacuo to afford (S)-4-(5-chloro-2,3-dihydrobenzofuran-7-yl)-1,1,1-trifluoro-4-methyl-2-p-tolylsulfanylmethylpentan-2-ol as a yellow oil (1.43 g, 99%).

To a solution of (S)-4-(5-chloro-2,3-dihydrobenzofuran-7-yl)-1,1,1-trifluoro-4-methyl-2-p-tolylsulfanylmethylpentan-2-ol (1.43 g, 3.21 mmol) in 10 mL of anhydrous dichloromethane was added trimethyloxonium tetrafluoroborate (713 mg, 4.82 mmol). The resulting suspension was stirred at room temperature for 4.5 hours. A solution of potassium carbonate (1.33 g, 9.64 mmol) in 10 mL of water was then added. After 13 hours, the reaction mixture was poured into 40 mL of saturated aqueous sodium bicarbonate solution and extracted with three 50 mL portions of dichloromethane. The combined organic phases were washed with brine, dried over magnesium sulfate, filtered, and concentrated in vacuo. Purification by column chromatography with silica gel (eluted with 0%-2% EtOAc/hexanes) afforded the title compound as a clear oil (974 mg, 95%).

Example 4

Synthesis of (R)-5-Bromo-7-[1,1-dimethyl-2-(2-trifluoromethyloxiranyl)ethyl]-2,3-dihydrobenzofuran

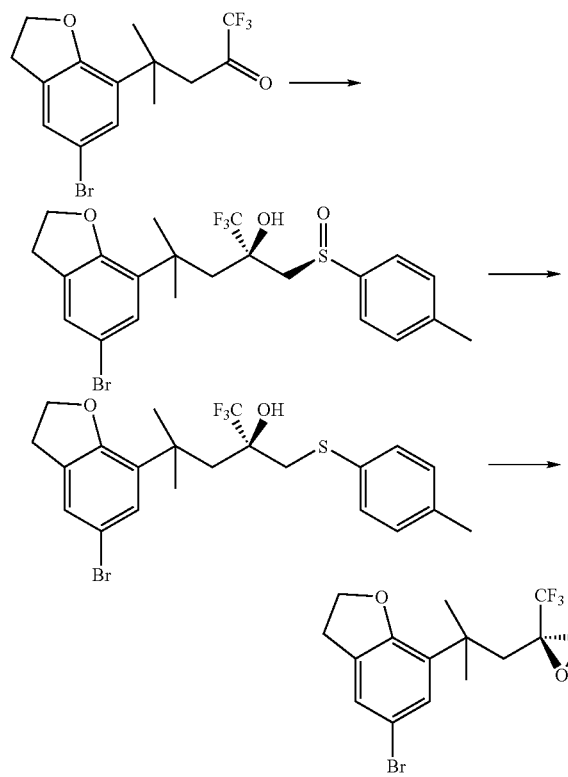

To a suspension of (R)-(+)-methyl p-tolylsulfoxide (8.80 g, 57.0 mmol) in 100 mL of anhydrous THF at −78° C. was added LDA mono(tetrahydrofuran) 1.5 M solution in cyclohexane (38.0 mL, 57.0 mmol) over 20 minutes. The resulting clear yellow solution was stirred for an additional 15 minutes. 4-(5-bromo-2,3-dihydrobenzofuran-7-yl)-1,1,1-trifluoro-4-methylpentan-2-one (18.2 g, 51.9 mmol) dissolved in 40 mL of THF was then added by cannula over 15 minutes. After 1 hour at −78° C., the reaction mixture was quenched with 300 mL of water and extracted with three 300 mL portions of EtOAc. The combined organic phases were washed with saturated aqueous sodium bicarbonate solution, then brine, dried over magnesium sulfate, filtered, and concentrated in vacuo. Purification by column chromatography with silica gel (eluted with 10%-25% EtOAc-hexanes) afforded sequentially (S)-4-(5-bromo-2,3-dihydrobenzofuran-7-yl)-1,1,1-trifluoro-4-methyl-2-((R)-toluene-4-sulfinylmethyl)pentan-2-ol (11.5 g, 44%) and (R)-4-(5-bromo-2,3-dihydrobenzofuran-7-yl)-1,1,1-trifluoro-4-methyl-2-((R)-toluene-4-sulfinylmethyl)pentan-2-ol (5.47 g, 21%).

The diastereomeric excess was determined to be >99% for both isomers (HPLC peak area).

To a suspension of (S)-4-(5-bromo-2,3-dihydrobenzofuran-7-yl)-1,1,1-trifluoro-4-methyl-2-((R)-toluene-4-sulfinylmethyl)pentan-2-ol (11.5 g, 22.8 mmol) and sodium iodide (10.2 g, 68.1 mmol) in 180 mL of anhydrous acetone at −40° C. was added a solution of trifluoroacetic acid anhydride (16.0 mL, 113 mmol) in 30 mL of anhydrous acetone dropwise by syringe over 20 minutes. A greenish brown mixture was formed instantaneously. After 20 minutes, the reaction mixture was quenched with saturated aqueous sodium sulfite solution and neutralized with saturated aqueous sodium carbonate solution. The brown color disappeared and the crude was concentrated to remove most of the acetone solvent. The resulting material was diluted with 350 mL of water and extracted with three 600 mL portions of ether. The combined organic phases were washed with brine, dried over magnesium sulfate, filtered, and concentrated in vacuo to afford (S)-4-(5-bromo-2,3-dihydrobenzofuran-7-yl)-1,1,1-trifluoro-4-methyl-2-p-tolylsulfanylmethyl-pentan-2-ol as a yellow oil (11.1 g, 99%).

To a solution of (S)-4-(5-bromo-2,3-dihydrobenzofuran-7-yl)-1,1,1-trifluoro-4-methyl-2-p-tolylsulfanylmethylpentan-2-ol (11.1 g, 22.6 mmol) in 75 mL of anhydrous dichloromethane was added trimethyloxonium tetrafluoroborate (5.18 g, 35.0 mmol). The resulting suspension was stirred at room temperature for 4.5 hours. A solution of potassium carbonate (9.40 g, 68.0 mmol) in 75 mL of water was then added. After 13 hours, the reaction mixture was poured into 200 mL of saturated aqueous sodium bicarbonate solution and extracted with three 300 mL portions of dichloromethane. The combined organic phases were washed with brine, dried over magnesium sulfate, filtered, and concentrated in vacuo. Purification by column chromatography with silica gel (eluted with 0%-2% EtOAc-hexanes) afforded the title compound as a clear oil (7.84 g, 95%).

We claim:

1. A process for stereoselective synthesis of a compound of Formula (X) or Formula (X')

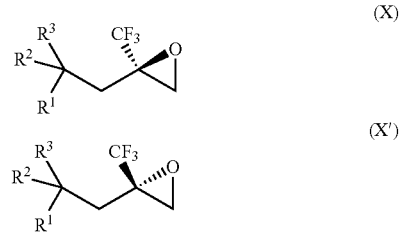

wherein:

R¹ is an aryl, heteroaryl, or $C_5$-$C_{15}$ cycloalkyl group, each optionally substituted with one to three substituent groups, wherein each substituent group of R¹ is independently $C_1$-$C_5$ alkyl, $C_2$-$C_5$ alkenyl, $C_2$-$C_5$ alkynyl, $C_3$-$C_8$ cycloalkyl, heterocyclyl, aryl, heteroaryl, $C_1$-$C_5$ alkoxy, $C_2$-$C_5$ alkenyloxy, $C_2$-$C_5$ alkynyloxy, aryloxy, acyl, $C_1$-$C_5$ alkoxycarbonyl, $C_1$-$C_5$ alkanoyloxy, $C_1$-$C_5$ alkanoyl, aroyl, aminocarbonyl, alkylaminocarbonyl, dialkylaminocarbonyl, aminocarbonyloxy, $C_1$-$C_5$ alkylaminocarbonyloxy, $C_1$-$C_5$ dialkylaminocarbonyloxy, $C_3$-$C_5$ cycloalkylaminocarbonyloxy, $C_1$-$C_5$ alkanoylamino, $C_1$-$C_5$ alkoxycarbonylamino, $C_1$-$C_5$ alkylsulfonylamino, aminosulfonyl, $C_1$-$C_5$ alkylaminosulfonyl, $C_1$-$C_5$ dialkylaminosulfonyl, halogen, hydroxy, carboxy, cyano, trifluoromethyl, trifluoromethoxy, nitro, or amino wherein the nitrogen atom is optionally independently mono- or di-substituted by $C_1$-$C_5$ alkyl or aryl; or ureido wherein either nitrogen atom is optionally independently substituted with $C_1$-$C_5$ alkyl or $C_3$-$C_5$ cycloalkyl; or $C_1$-$C_5$ alkylthio, wherein each substituent group of $R^1$ is optionally independently substituted with one to four substituent groups selected from aryl or heterocyclyl wherein the heterocycle is optionally independently substituted with hydroxyl, halogen, methyl, or dialkylamino; $C_1$-$C_5$ alkoxycarbonyl, methyl, methoxy, halogen, hydroxy, oxo, cyano, aminosulfonyl, or amino wherein the nitrogen atom is optionally independently mono- or di-substituted by $C_1$-$C_5$ alkyl or $C_1$-$C_3$ dialkylamine or aryl; or ureido wherein either nitrogen atom is optionally independently substituted with $C_1$-$C_5$ alkyl; or oxime wherein the oxygen atom is optionally substituted by $C_1$-$C_5$ alkyl or benzyl;

$R^2$ and $R^3$ are each independently hydrogen, $C_1$-$C_5$ alkyl, or $C_5$-$C_{15}$ arylalkyl group, or $R^2$ and $R^3$ together with the carbon atom they are commonly attached to form a $C_3$-$C_8$ spiro cycloalkyl ring, or $R^1$ and $R^2$ when taken together are a chromanyl or dihydrobenzofuranyl optionally substituted with $C_1$-$C_5$ alkyl, $C_2$-$C_5$ alkenyl, $C_2$-$C_5$ alkynyl, $C_3$-$C_8$ cycloalkyl, heterocyclyl, aryl, heteroaryl, $C_1$-$C_5$ alkoxy, $C_2$-$C_5$ alkenyloxy, $C_2$-$C_5$ alkynyloxy, aryloxy, acyl, $C_1$-$C_5$ alkoxycarbonyl, $C_1$-$C_5$ alkanoyloxy, aminocarbonyl, alkylaminocarbonyl, dialkylaminocarbonyl, aminocarbonyloxy, $C_1$-$C_5$ alkylaminocarbonyloxy, $C_1$-$C_5$ dialkylaminocarbonyloxy, $C_1$-$C_5$ alkanoylamino, $C_1$-$C_5$ alkoxycarbonylamino, $C_1$-$C_5$ alkylsulfonylamino, aminosulfonyl, $C_1$-$C_5$ alkylaminosulfonyl, $C_1$-$C_5$ dialkylaminosulfonyl, halogen, hydroxy, carboxy, oxo, cyano, trifluoromethyl, trifluoromethoxy, trifluoromethylthio, nitro, or amino wherein the nitrogen atom is optionally independently mono- or di-substituted by $C_1$-$C_5$ alkyl; or ureido wherein either nitrogen atom is optionally independently substituted with $C_1$-$C_5$ alkyl; or $C_1$-$C_5$ alkylthio wherein the sulfur atom is optionally oxidized to a sulfoxide or sulfone, the process comprising:

(a) reacting the starting material of formula A with a chiral sulfoxide anion source B or B', where R is an alkyl or aryl group and M is a counter-cation, in a suitable solvent to prepare a compound of formula C or C', respectively (b) reducing the sulfoxide of formula C or C' in a suitable solvent to obtain the compound of formula D or D', respectively (c) cyclizing the compound of formula D or D' in a suitable solvent to form the epoxide compound of Formula (X) or Formula (X'), respectively

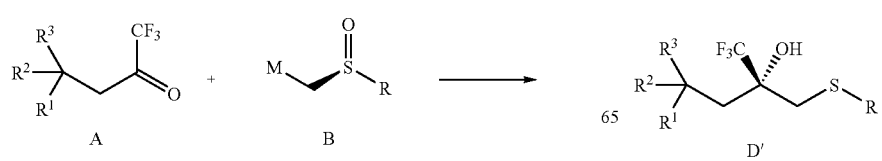

-continued

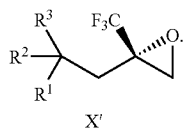

2. The process according to claim 1, wherein:
$R^1$ is an aryl or heteroaryl group, each optionally substituted with one to three substituent groups,
  wherein each substituent group of $R^1$ is independently $C_1$-$C_5$ alkyl, $C_2$-$C_5$ alkenyl, $C_2$-$C_5$ alkynyl, $C_3$-$C_8$ cycloalkyl, heterocyclyl, aryl, heteroaryl, $C_1$-$C_5$ alkoxy, $C_2$-$C_5$ alkenyloxy, $C_2$-$C_5$ alkynyloxy, aryloxy, $C_1$-$C_5$ alkanoyloxy, $C_1$-$C_5$ alkanoyl, aroyl, halogen, hydroxy, trifluoromethyl, trifluoromethoxy, or $C_1$-$C_5$ alkylthio,
    wherein each substituent group of $R^1$ is optionally independently substituted with one to three substituent groups selected from methyl, methoxy, fluoro, chloro, or hydroxy; and
$R^2$ and $R^3$ are each independently hydrogen or $C_1$-$C_5$ alkyl, or $R^2$ and $R^3$ together with the carbon atom they are commonly attached to form a $C_3$-$C_8$ spiro cycloalkyl ring.

3. The process according to claim 1, wherein the suitable solvent of step (a) is diethyl ether, dipropyl ether, diisopropyl ether, dibutyl ether, tetrahydrofuran (THF), ethylene glycol dimethyl ether (DME), tert-butyl methyl ether (MTBE), or a mixture thereof.

4. The process according to claim 1, wherein the chiral sulfoxide anion source B is generated from the corresponding neutral sulfoxide precursor with a base selected from lithium diisopropylamide (LDA), sodium hexamethyldisilazide (NaHMDS), potassium hexamethyldisilazide (KHMDS), sodium hydride, potassium hydride, n-butyllithium, methyllithium, ethyl magnesium bromide, and methylmagnesium bromide.

5. The process according to claim 1, wherein the reduction of step (b) is accomplished using a reducing agent selected from lithium aluminum hydride (LAH), diisobutyl aluminum hydride (DIBAL), or a 65 wt. % solution of sodium bis(2-methoxyethoxy)aluminum hydride in toluene (Red-Al®).

6. The process according to claim 1, wherein the reduction of step (b) is accomplished using trifluoroacetic acid anhydride/sodium iodide, trifluoroacetic acid anhydride/2,4,6-trimethylpyridine, or hydrogen chloride in ethanol.

7. The process according to claim 1, wherein the suitable solvent of step (b) is diethyl ether, toluene, tetrahydrofuran (THF), tert-butyl methyl ether (MTBE), hexanes, benzene, acetonitrile, acetone, dichloromethane, ethyl acetate, or a mixture thereof.

8. The process according to claim 5, wherein the suitable solvent of step (b) is diethyl ether, toluene, tetrahydrofuran (THF), tert-butyl methyl ether (MTBE), hexanes, or a mixture thereof.

9. The process according to claim 6, wherein the suitable solvent of step (b) is toluene, benzene, acetonitrile, acetone, dichloromethane, ethyl acetate, THF, diethyl ether, or a mixture thereof.

10. The process according to claim 1, wherein the cyclization of step (c) is accomplished using an alkylating agent.

11. The process according to claim 10, wherein the alkylating agent is an alkyl halide or a trialkyloxonium reagent.

12. The process according to claim 10, wherein the alkylating agent is methyl iodide, methyl bromide, ethyl iodide, trimethyloxonium tetrafluoroborate, trimethyloxonium hexachloroantimonate, triethyloxonium tetrafluoroborate, triethyloxonium hexafluorophosphate, or triethyloxonium hexachloroantimonate.

13. The process according to claim 1, wherein the suitable solvent of step (c) is dichloromethane, chloroform, dichloroethane, tetrahydrofuran (THF), diethyl ether, toluene, benzene, ethyl acetate, or a mixture thereof.

14. The process according to claim 1, wherein the cyclization of step (c) is accomplished with a suitable organic or inorganic base.

15. The process according to claim 14, wherein the suitable organic or inorganic base is triethylamine (TEA), diisopropylethylamine (DIEA), pyridine, lutidine, sodium hydride, potassium hydride, potassium carbonate, or sodium carbonate.

* * * * *